US011051722B2

(12) United States Patent
Katisko et al.

(10) Patent No.: US 11,051,722 B2
(45) Date of Patent: Jul. 6, 2021

(54) APPARATUS FOR AND METHOD OF MONITORING MOVEMENT

(71) Applicant: HEAD INSTRUMENTS OY, Oulu (FI)

(72) Inventors: Jani Katisko, Oulu (FI); Ossi Kumpula, Oulu (FI)

(73) Assignee: HEAD INSTRUMENTS OY, Oulu (FI)

( * ) Notice: Subject to any disclaimer, the term of this patent is extended or adjusted under 35 U.S.C. 154(b) by 17 days.

(21) Appl. No.: 16/665,539

(22) Filed: Oct. 28, 2019

(65) Prior Publication Data

US 2020/0138339 A1 May 7, 2020

(30) Foreign Application Priority Data

Nov. 2, 2018 (GB) .................................. 1817974.7

(51) Int. Cl.
*G06K 9/00* (2006.01)
*A61B 5/11* (2006.01)
(Continued)

(52) U.S. Cl.
CPC .......... *A61B 5/1128* (2013.01); *A61B 5/0022* (2013.01); *G06T 7/0012* (2013.01);
(Continued)

(58) Field of Classification Search
CPC .......... A61B 2562/0219; A61B 5/0022; A61B 5/1101; A61B 5/1128; A61B 5/117;
(Continued)

(56) References Cited

U.S. PATENT DOCUMENTS 5,573,011 A 11/1996 Felsing
8,187,209 B1 5/2012 Giuffrida
(Continued)

FOREIGN PATENT DOCUMENTS

WO 2005/109847 11/2005
WO 2009/149520 12/2009
(Continued)

OTHER PUBLICATIONS

Extended European Search Report dated Dec. 17, 2019 in corresponding European Application No. 19206381, 3 pages.
(Continued)

*Primary Examiner* — Tom Y Lu
(74) *Attorney, Agent, or Firm* — Nixon & Vanderhye PC

(57) ABSTRACT

Apparatus comprises an acceleration unit, a processing unit and a display for continuous real time monitoring. The acceleration unit is attached or held by a body region of a mammal comprises a 3D-acceleration sensor and a wireless transmitter for transmitting a measurement signal provided by the acceleration sensor continuously. The processing unit processes the measurement signal continuously in a band of a medically defined movement of the body region, forms a movement index on the basis of a norm of values of acceleration in a first time window, and forms a value(s) of amplitude, and/or a value of frequency of the spatial movement of the body region on the basis of a power spectral density in second time window of a known duration. The display displays said movement index with said value of amplitude, and/or said value of frequency of the spatial movement continuously in real time.

18 Claims, 4 Drawing Sheets

(51) Int. Cl.
*A61B 5/00* (2006.01)
*G06T 7/00* (2017.01)
*G06T 7/20* (2017.01)

(52) U.S. Cl.
CPC ........ *G06T 7/20* (2013.01); *A61B 2562/0219* (2013.01); *G06T 2207/10016* (2013.01)

(58) Field of Classification Search
CPC ........... A61B 5/4082; A61B 5/68; A61B 5/72; G06T 2207/10016; G06T 7/0012; G06T 7/20
See application file for complete search history.

(56) References Cited

U.S. PATENT DOCUMENTS

| | | | | |
|---|---|---|---|---|
| 2010/0030119 | A1* | 2/2010 | McNames | A61B 5/1101 600/595 |
| 2013/0060124 | A1 | 3/2013 | Zietsma | |
| 2016/0220151 | A1* | 8/2016 | Zizi | A61B 5/1101 |
| 2017/0286658 | A1 | 10/2017 | Zamfir et al. | |
| 2019/0076203 | A1* | 3/2019 | Ang | A61B 90/20 |
| 2019/0206566 | A1* | 7/2019 | Lai | A61B 5/1124 |

FOREIGN PATENT DOCUMENTS

| | | |
|---|---|---|
| WO | 2016/133621 | 8/2016 |
| WO | 2016/133631 | 8/2016 |

OTHER PUBLICATIONS

Combined Search and Examination Report dated Dec. 21, 2018 in corresponding Application No. GB1817974.7, 10 pages.
Examination Report dated Nov. 21, 2019 in corresponding Application No. GB1817974.7, 3 pages.
Intention to Grant dated Sep. 18, 2020 in corresponding Application No. GB1817974.7, 2 pages.
Search Report for GB1817974.7, dated Dec. 20, 2018, 2 pages.
Elble et al., "Using Portable Transducers to Measure Tremor Severity", Tremor and Other Hyperkinetic Movements, published May 17, 2016, 12 pages.
Examination Report dated Nov. 21, 2019 in corresponding GB Application No. 18179747, 3 pages.

* cited by examiner

APPARATUS FOR AND METHOD OF MONITORING MOVEMENT

This application claims priority to GB Patent Application No. 1817974.7 filed 2 Nov. 2018, the entire contents of which is hereby incorporated by reference.

FIELD

The invention relates to an apparatus for and a method of monitoring movement.

BACKGROUND

Involuntary movement of a body region, which may be oscillatory and can often be considered tremor, is a common and frustrating disorder. Visual observation by a neurologist dominates an assessment of the movement of a body region in clinical practice. All people, healthy or disordered, have tremor at some extent and determination of its development over time or under treatment is not possible, because a movement of a body region of a person or animal at one moment cannot reliably be compared with that of another moment. Although technical measurements of the movement of a body region have been attempted, they are complicated, inefficient and insufficient. Hence, there is a need to improve the monitoring.

BRIEF DESCRIPTION

The invention is defined by the independent claims. Embodiments are defined in the dependent claims.

LIST OF DRAWINGS

Example embodiments of the present invention are described below, by way of example only, with reference to the accompanying drawings, in which FIG. 1 illustrates an example of a movement monitoring apparatus;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned. All combinations of the embodiments are considered possible if their combination does not lead to structural or logical contradiction.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

An involuntary movement of a body region, which is well defined in medicine, may include tremor, and it may include a linear transition or displacement and/or rhythmic shaking of the body region. The movements may be regular or irregular. The body region may refer to a limb, a finger, a paw a hand, an arm, a leg, a foot, a toe or a head, for example. In a case, the body region may refer to the whole body. The involuntary movement may include involuntary oscillatory movement like the tremor which is found in every living mammal. The involuntary oscillatory movement of a healthy mammal is typically hardly noticeable while a mammal having a pathological condition may have a movement disorder that is devastating. There is a variety of medically defined tremors such as action tremor, resting tremor, or postural tremor, for example.

A frequency band of the involuntary movement is well defined in the medicine, and the band may be between 0 Hz and 30 Hz for example without limiting to this. A non-oscillatory movement of a body region can also be represented by Fourier frequencies. A low frequency oscillatory movement of a body region may be considered to take place below 4 Hz. A medium frequency oscillatory movement of a body region may be considered to take place between 4 Hz and 7 Hz. A high frequency oscillatory movement of a body region may be considered to take place between 7 Hz and 30 Hz. For example, a Parkinsonian oscillatory movement of a body region may take place in frequencies between 3 Hz to 7 Hz.

Figure 1:
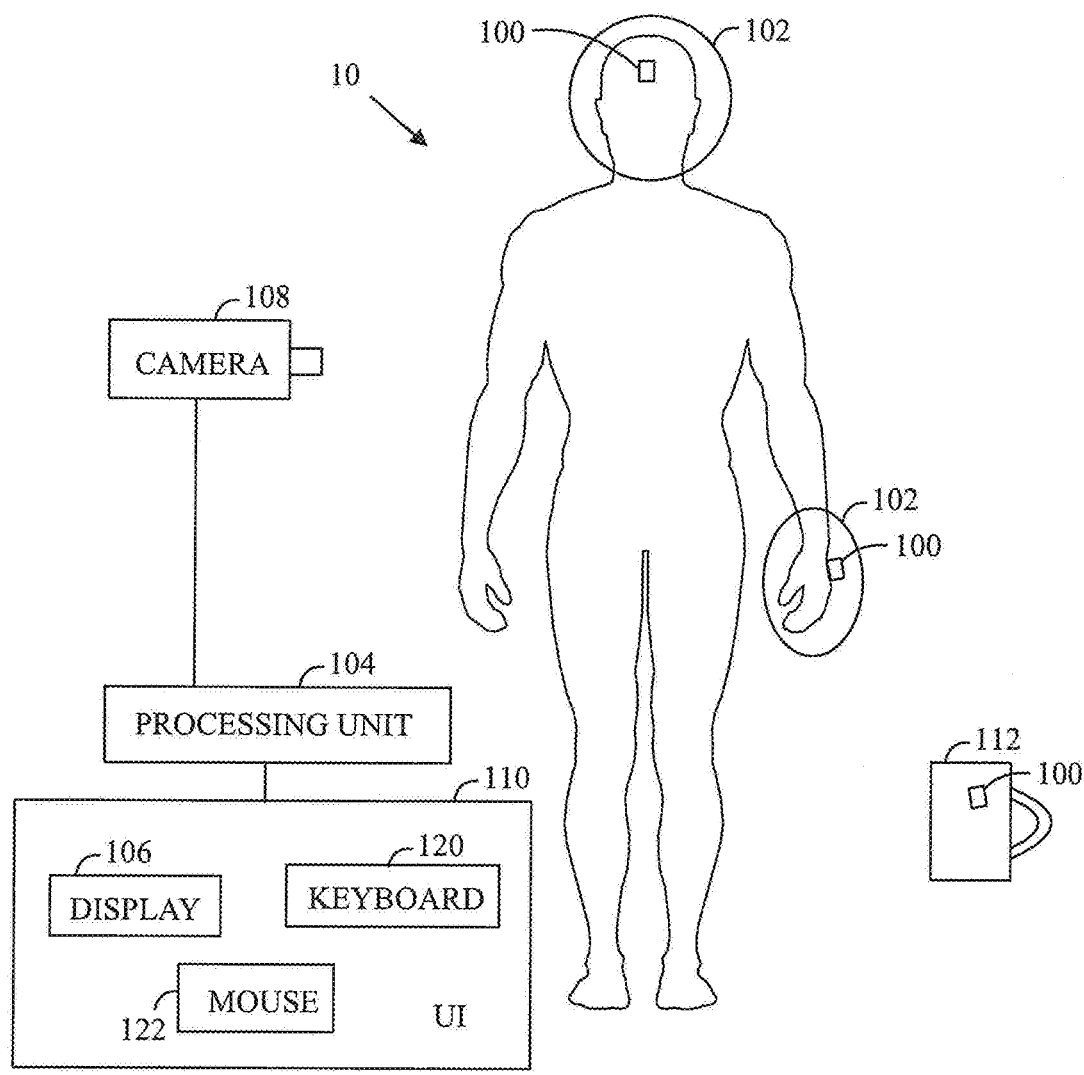

FIG. 1 illustrates an example of a movement monitoring apparatus that performs continuous real time monitoring of a mammal.

An acceleration unit 100 of the movement monitoring apparatus is attachable to or holdable by a body region 104 of a mammal 10. The mammal 10 may be a human being or an animal. The animal may be a pet, a livestock mammal, a wild animal or an animal in a zoo. The animal may be a mouse, a rat, a cat, a dog, a horse, a cow, a pig, a lamb, an elephant, a lion, a tiger or the like, for example. The acceleration unit 100 may be attached to the skin of the mammal 10 by glue or a tape. The acceleration unit 100 may also be bound to the mammal 10 with straps, for example. The acceleration unit 100 may be attached to a carrier 112, which is attachable to or holdable by the mammal 10. The acceleration unit 100 may be attached to the carrier 112 by glue or a tape. The carrier may be held in hand or in mouth. The carrier may be a mug, a glass, a fork, a spoon, a knife, a plate, a tooth brush, a brush, a pen, a pencil, scissors, a remote controller, a mobile communication device, a camera, a piece of material like a plate, which can be held with one hand, or the like, for example.

Figure 2:
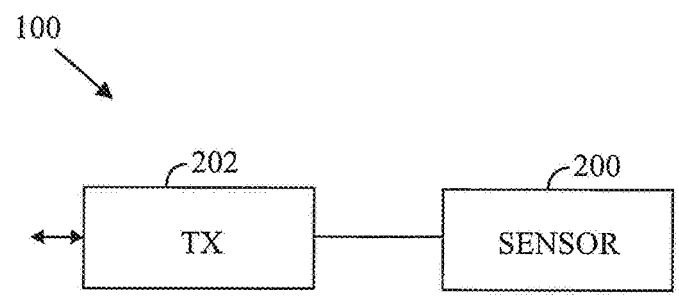
FIG. 2 illustrates an example of an acceleration unit.

The acceleration unit 100, an example of which is illustrated in FIG. 2, comprises a three-dimensional acceleration sensor 200, which is known to a person skilled in the art, per se, and a wireless transmitter 202 for transmitting a measurement signal provided by the acceleration sensor 200 continuously. The measurement signal carries three-dimensional information about acceleration of the body region 102. An application programming interface, which has one or more communication protocols takes care of the wireless communication. A measurement range of the acceleration sensor 200 may be about +/−8 G, for example without limiting to that. Here the unit G refers to the G-force acceleration experienced by the acceleration unit 100. An acceleration of 1 G refers to acceleration caused by a standard gravity which corresponds to the gravity of the earth. A sampling rate of the acceleration sensor 200 may be about 100 Hz, for example without limiting to that. The acceleration unit 100 may comprise a timer and the samples i.e. values of acceleration may be timestamped. The acceleration unit 100 may be splash-proof or water-proof.

A processing unit 104 of the movement monitoring apparatus receives the measurement signal and processes the measurement signal continuously in a band of a movement of the body region defined in medicine. The processing unit 104 forms a movement index on the basis of a norm of values of acceleration in a first time window of a known duration. The processing unit 104 forms a value of amplitude of spatial movement of the body region on the basis of a power spectral density in second time window of a known duration. The spatial movement takes place in space of dimensions of height, depth and width, and may be measured in SI units of length such as millimeters (SI=Standard of Units). Alternatively, the processing unit 104 forms a value of frequency of the spatial movement on the basis of a power spectral density in second time window of a known duration. The frequency may be the same as the frequency of the measured signal. The processing unit 104 may also form a value of amplitude of the spatial movement and a value of frequency of the spatial movement on the basis of a power spectral density in second time window of a known duration. The movement index and the value of amplitude of the spatial movement and/or frequency of the measurement defines the movement in a unique manner for one mammal 10, and allows a reliable comparison therebetween when a plurality of measurements them are performed at different moments.

The norm may be formed from sample values as an L1-norm which can be applied in an Euclidian geometry. The norm may be formed from sample values using an inner product, which may be a dot product. The norm may be formed by squaring values of the three dimensions, summing the squared values together and taking a positive square root of the sum, $Np=(x^2+y^2+z^2)^{0.5}$, where Np is a norm of a $p^{th}$ sample, x is a value of acceleration in x-direction, y is a value of acceleration in y-direction, and z is a value of acceleration in z-direction.

An operation may be applied to a plurality of the thus formed norms of the first time window to form a representative norm of them. The norms of the first window may be averaged. Alternatively or additionally, a mean may be formed.

The norm may be scaled with a coefficient or used as an argument of a function for forming the movement index. However, the norm as such may also be used as the movement index.

A display 106 in a user interface 110 of the movement monitoring apparatus presents said movement index with said value of amplitude and/or said value of frequency of the measurement signal continuously in real time.

In an embodiment, only peaks of the movement the half strength width of which is equal to or narrower than about 2 Hz are utilized in the measurement of the movement index. This effectively limits volational movements outside the monitoring and improves reliability of the monitoring.

In an embodiment, a measurement of the movement of a body region 102 may be performed between 1 Hz to 30 Hz. In an embodiment, a measurement of the movement of a body region 102 may be performed between 2 Hz to 25 Hz. In an embodiment, a measurement of the movement of a body region may be performed between 3 Hz to 20 Hz.

The data transfer of the movement monitoring apparatus is fast enough for the real time operation. A real time system refers to a system a response of which takes place without significant delay with respect to a human reaction time. In a system operation in real time, an input signal may be processed and a response may be output within about one second which allows a practically immediate feedback to the input signal, where the immediate feedback refers to a quickest human response which may be considered to be between about a tenth of a second and one second. That is, the movement monitoring apparatus can present information about the measured acceleration in about one second from the measurement.

The real time data transfer is an important feature during a surgical intervention such as thalamotomy for relieving essential tremor or the like, for example. When a surgeon searches for a most effective, precise location in a brain to deliver electrical pulses that affect the tremor using deep brain stimulation, the display 106 of the movement monitoring apparatus can show the surgeon said movement index with said value of amplitude of the spatial movement and/or said value of frequency of the spatial movement measured from the body region continuously in real time. After testing a plurality of locations in the brain, the surgeon can determine exactly where the deep brain stimulation resulted in the most effective or suitable tremor relief. The electrical pulses of the deep brain stimulation device, which may be a battery-operated neurotransmitter, cancel fully or partly the tremor when connected at the found location of the brain.

Another application of the movement monitoring apparatus may be related to a magnetic resonance encephalography or the like. Capturing a magnetic resonance image takes a rather long time and may take even about 30 minutes. During the imaging the patient must be immobile. However, when the patient is inside the magnetic resonance encephalography apparatus, it is impossible or challenging to observe whether the patient moves or not. If only the magnetic resonance image shows that the patient has moved too much during imaging and the image is useless, it is waste of resources and money. But if the patient is a user of the acceleration unit 100, it is possible to monitor the patient in the magnetic resonance encephalography apparatus in real time. If the patient moves in an undesirable manner soon after the magnetic resonance imaging has started (after about 3 minutes from starting the magnetic resonance imaging lasting about 30 minutes, for example), a lot of the imaging time (about 27 minutes) and energy can be saved by stopping the original magnetic resonance imaging and starting the magnetic resonance imaging again right after observing the undesirable movement.

Because the acceleration unit 100 is easy to attach to the body region and the movement monitoring apparatus as a whole is easy to use, a user can measure his/her or his/her mammal's 10 movement index, value of amplitude and/or value of frequency of the spatial movement at home. The user only needs at least one acceleration unit 100 and a computer with a suitable computer program. The communication between the acceleration unit 100 and the computer including the processing unit 104 may be performed using a wireless local access network (WLAN) or Wi-Fi ("Wireless Fidelity", IEEE 802.11). Additionally or alternatively the wireless communication the acceleration unit 100 and the processing unit 104 may be based on Bluetooth or 5G NR (5. Generation New Radio). A magnetic, ultrasound and/or optical communication is also possible.

The processing unit 104 may be a computer, and the user interface 110 of the movement monitoring apparatus may comprise a keyboard 120 and a mouse 122. Alternatively or additionally, the display 106 may be a touch screen.

In an embodiment, the processing unit 104 may associate an identification of the mammal 10 with each of said movement index and said value of amplitude and/or said value of frequency. The display 104 may display the identification and said movement index with said value of amplitude and/or said value of frequency of the spatial movement. The identification may include a name and/or a unique code.

In an embodiment, a maximum total mass of the at least one acceleration unit 100 attached to the body region 102 may be about 10% of a mass of the body region 102. For example, a human head may weight about 5 kg. An arm of a human may be estimated to weight about 5% to 6% of the total body weight of a person.

In an embodiment, a maximum total mass of the at least one acceleration unit 100 attached to a body region 102 is about 5% of a mass of the body region 102.

In an embodiment, a maximum mass of the at least one acceleration unit 100 is 50 g. The acceleration unit 100 can be made light i.e. the mass may be equal to or less than 50 g because there are available acceleration sensors and wireless transmitters that are lighter than 50 g in the market. The acceleration unit can be made to have a mass of 1 g, for example. The acceleration unit can be made to have a mass of about 5 g, for example. The acceleration unit can be made to have a mass of about 10 g, for example. The acceleration unit can be made to have a mass of about 20 g, for example.

In an embodiment, the first time window is between about half a second and two seconds, and the second time window is between one second and ten seconds, respectively. The second window may be longer than the first time window.

In an embodiment, the apparatus may comprise a camera 108 for capturing a video of the mammal 10, the movement of which is monitored. The processing unit 104 may store and associate the video with the movement index and/or the identification of the mammal 10. The display 106 may present said video, and said movement index with said value of amplitude and/or said value of frequency of the spatial movement synchronously with the video. A video may be a sequence of electronically captured images, which may be stored, presented and replayed. Sufficient rapidity (about 30 frames per second, for example) in capturing, presentation or replaying of the sequence results in the illusion of continuous motion.

The presentation of the video with the movement index and said value of amplitude and/or said value of frequency of the spatial movement may be performed during the measurement or later. For the later presentation the video with the movement index and said value of amplitude and/or said value of frequency of the spatial movement may be stored in memory of the processing unit 104 or in some other, remote memory. The remote memory may be in a server such as a cloud server, for example.

In an embodiment, the processing unit 104 may store said movement index and said value of amplitude and/or said value of frequency formed on the basis of measurements at a plurality of moments, and present said movement index and said value of amplitude and/or said value of frequency formed at a moment and said movement index and said value of amplitude and/or said value of frequency formed at a different moment for comparison. In this manner, the development or trend of the movement, which may be involuntary, can be determined over the time. A tremor may be treated, or it may cure or worsen naturally over time. The movement index may give an instant estimate of the state of the tremor at two separate moments.

Figure 3:
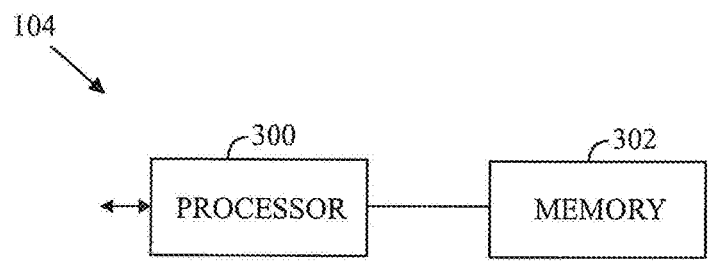
FIG. 3 illustrates an example of a processing unit.

In an embodiment an example of which is shown in FIG. 3, the processing unit 104 may comprise one or more processors 200, and one or more memories 202 including computer program code. The one or more memories 202 and the computer program code may, with the one or more processors 200, cause the apparatus at least to form the movement index on the basis of the norm of the values of acceleration in a first time window of the known duration, and form the value of the amplitude and/or the value of the frequency of the spatial movement on the basis of the power spectral density in the second time window of the known duration.

In an example embodiment, the transmitter 202 of the processing unit 104 may communicate with various radio communication networks such as any mobile phone network, regardless of the generation. In this manner, the processing unit 104 may send the data about the movement index with said value of amplitude and/or said value of frequency of the spatial movement over the Internet to a health center, a hospital, at least one health care professional or the like. The sent information, which may include video and/or identification, may be stored in a data bank. The sent information may be evaluated or assessed, and a condition of the measured mammal 10 may be diagnosed by the health care professional(s). This may be a real time data transfer or the sent information may be replayed and/or processed later.

In an example embodiment, the processing unit 104 may communicate using the transmitter 202 with a mobile communication device like a mobile phone using WLAN or Bluetooth or the like wireless communication method. The mobile communication device, in turn, may communicate with the various radio communication networks. Also in this manner, the processing unit 104 may send the data about the movement index with said value of amplitude and/or said value of frequency of the spatial movement over the Internet to a health center, a hospital, at least one health care professional or the like for a further processing like in the case the processing unit 104 communicates with the various radio communication networks directly.

Figure 4:
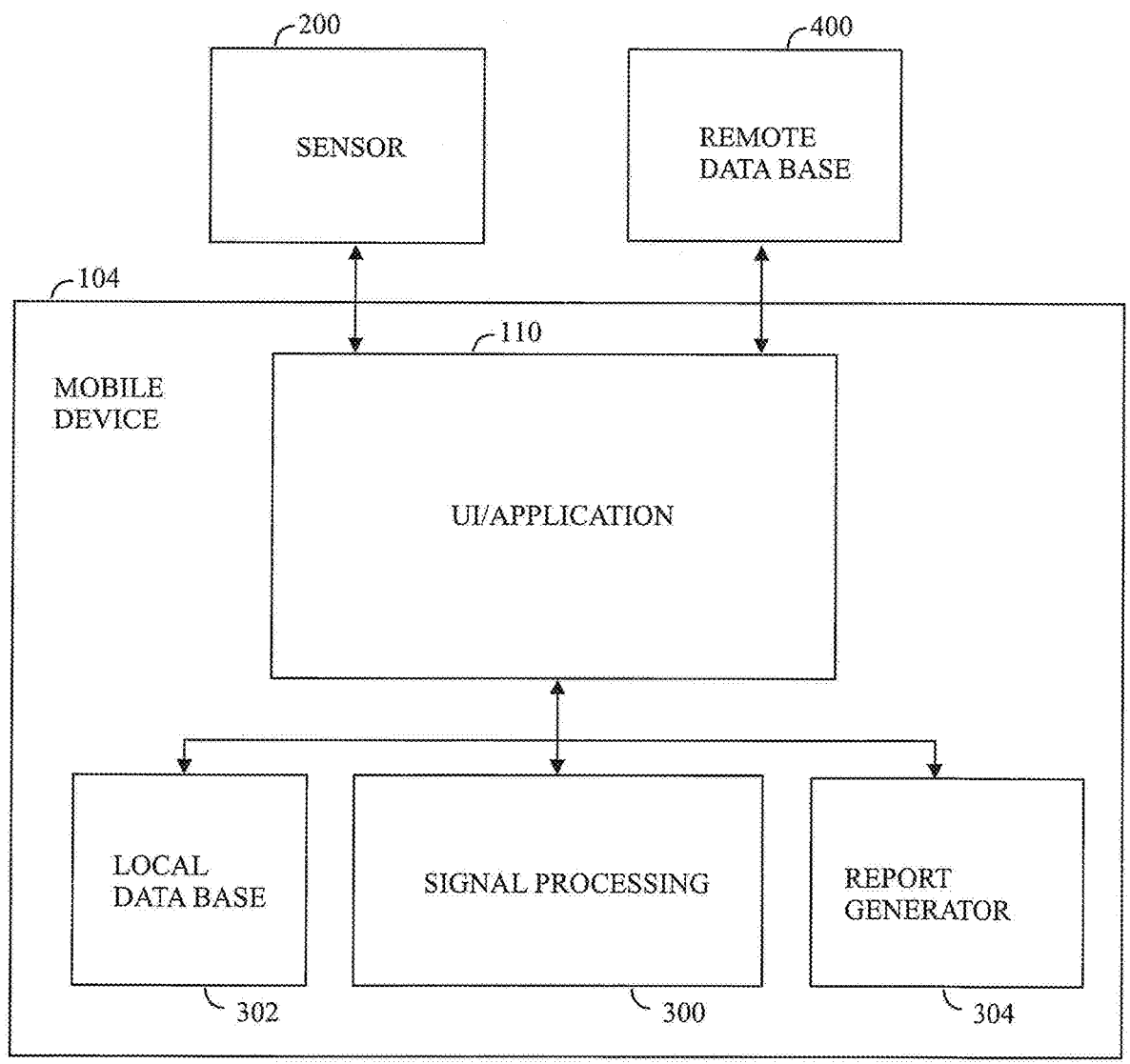
FIG. 4 illustrates an example of the movement monitoring apparatus, which is connected to a remote database.

FIG. 4 illustrates an example of the apparatus for monitoring movement, which is connected to a remote database 400 which may reside in a cloud. The remote database 400 may receive and store raw data, processed data and/or report data, for example. The remote database 400 may deliver the data stored therein for browsing in the user interface 110. The remote database 400 may also be used for storing backup. The monitoring apparatus may form real-time video and data graphics because the processing unit 104 may be connected with the camera 108 and the screen 104 where time domain graphs and identification of the measured mammal may be shown. Additionally, a starting moment of a possible treatment for a disorder and a present moment may be shown on the screen 106. An elapsed time from a start of a possible treatment may additionally or alternatively be shown. At the end of a measurement, a report of the measurement may be generated in the processing unit 104 and presented (display 106) and/or printed (printer 304). The report may include measured and processed acceleration values, graphs and videos time synchronized with the measured and processed values, for example.

The processing unit 300 performs the data processing with at least one processing algorithm for providing the movement index (movement disorder index) and a frequency domain graph. The processing unit 300 may perform real-time processing of the measurement signal provided by the acceleration unit 100.

The measurement data, a possible video and possible other data such as voice may be saved in a local database which may be the memory 302. The local database 302 may receive and store raw data, processed data and/or report data, for example. The local database 302 may deliver the data stored therein for browsing in the user interface 110. The saved data of the previous measurements may browsed and a list of previous measurements may be presented on the display 106. The saved measurements may be set as a shadow background for two-dimensional graphs. Any previous saved measurement may be compared with any other saved measurement. The comparison may be performed between measurements of the same mammal 10. The comparison may be refrained if the comparison is to be performed between measurements of different mammals 10. The processing unit 104 may form at least one trend parameter of the movement on the basis of said movement index of the measurement signal. The processing unit 104 may form at least one trend parameter of the movement on the basis of said value of amplitude of the spatial movement. The processing unit 104 may form at least one trend parameter of the movement on the basis of said value of frequency of the measurement signal.

The processing unit 104 may form at least one trend parameter of the movement on the basis of said movement index with said value of amplitude of the spatial movement. The processing unit 104 may form at least one trend parameter of the movement on the basis of said movement index with said value of frequency of the measurement signal.

The processing unit 104 may form at least one trend parameter of the movement on the basis of said movement index with said value of amplitude and/or said value of frequency of the spatial movement.

The trend parameter may represent a development of the movement as a function of time. That is, the movement may be gaining strength, may be maintaining unchanged or it may be settling down.

The apparatus for monitoring movement may be considered as a digital real-time meter for quantitative monitoring of movement disorders, and the apparatus enables an analysis of development of the condition/disorder and efficiency of the treatments.

Healthcare professionals and/or the user may monitor the symptoms of the movement in real time, and the stored information may be replayed or repeatedly shown to the healthcare professionals and/or the user. Measurements may be performed to follow the symptoms of the user or his/her mammal 10 and for a research/device development purpose.

Figure 5:
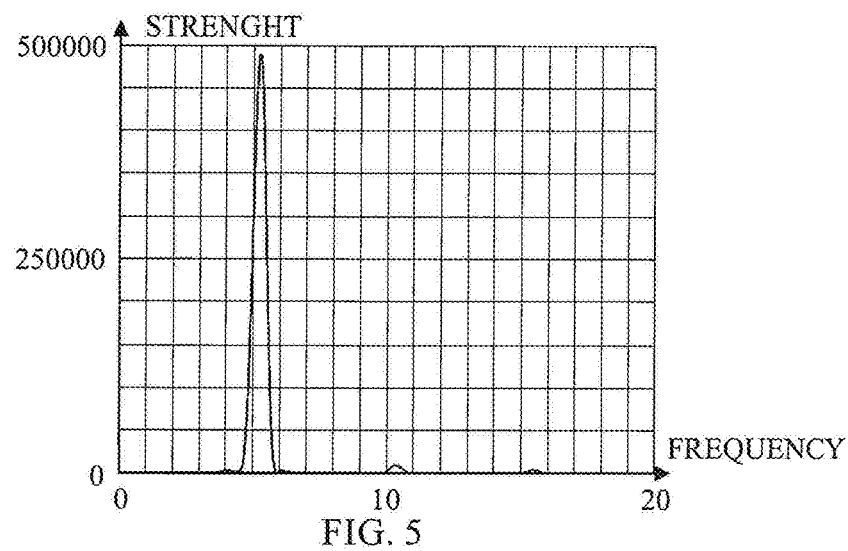
FIG. 5 illustrates an example of a periodogram.

FIG. 5 illustrates an example of a periodogram of the measured signal. The vertical axis is strength ($mG^2/Hz$) and the horizontal axis is frequency (Hz). It can be seen that there is a frequency peak at about 5.3 Hz. The maximum value of the 5.3 Hz peak is about 480000 $mG^2/Hz$. Amplitude of movement may be formed using peaks of the periodogram. A common periodogram of the three orthogonal directions may be formed using the L1-norm. Then peaks, a width of each of which is smaller than about 2 Hz (or some other limit), may be searched for, and an area of each of the peaks may be computed. Each of the areas corresponds to an RMS-amplitude of the measured signal (RMS=Root Mean Square). Then a spatial RMS-amplitude may be computed on the basis of an equation of a harmonic oscillation (which is known by a person skilled in the art, and a simple form of which is $md^2x/dt^2=-kx$, where k is a constant, m is a mass, x is a spatial dimension and t is time), and values of different peaks may be summed together. Finally, the values may be scaled as peak-to-peak amplitudes.

Figure 6:
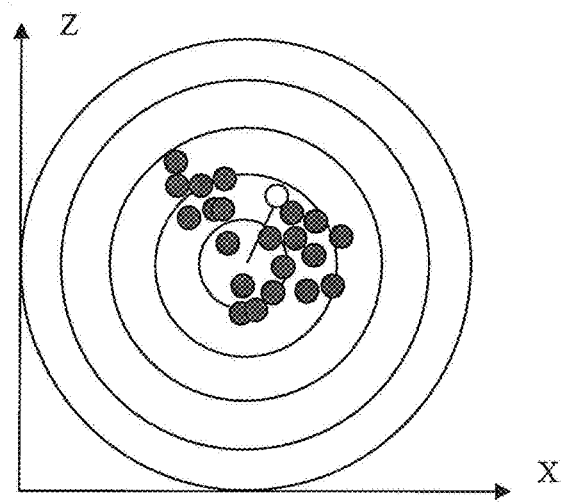
FIG. 6 illustrates an example of acceleration samples in x- and z-directions.
Figure 7:
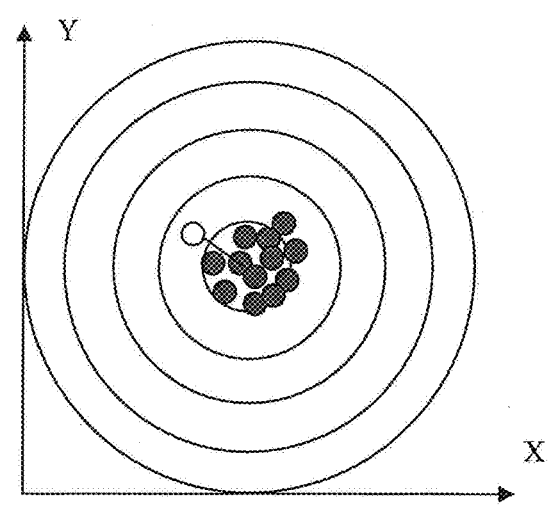
FIG. 7 illustrates an example of acceleration samples in x- and y-directions.

FIG. 6 illustrates an example of sample values of acceleration in z- and x-directions. FIG. 7 illustrates an example of sample values of acceleration in y- and x-directions, the directions x, y and z being orthogonal with respect to each other. Each dot is a measured value. The nested rings represent 2000, 4000, 6000, 8000 and 10000 mG accelerations while the common center of the rings refer to 0 mG. The norm Np of a sample p may be written as $Np=(1200^2+380^2+257^2)^{0.5}=1285$ mG, where 1200 mG may be acceleration in x-direction, 380 mG may be acceleration in y-direction and 257 mG may be acceleration in z-direction. The value 1285 mG may be used as the movement index. The graphs of FIGS. 5 to 7 may be presented in the display 106 when the measurements are made and during a replay.

Figure 8:
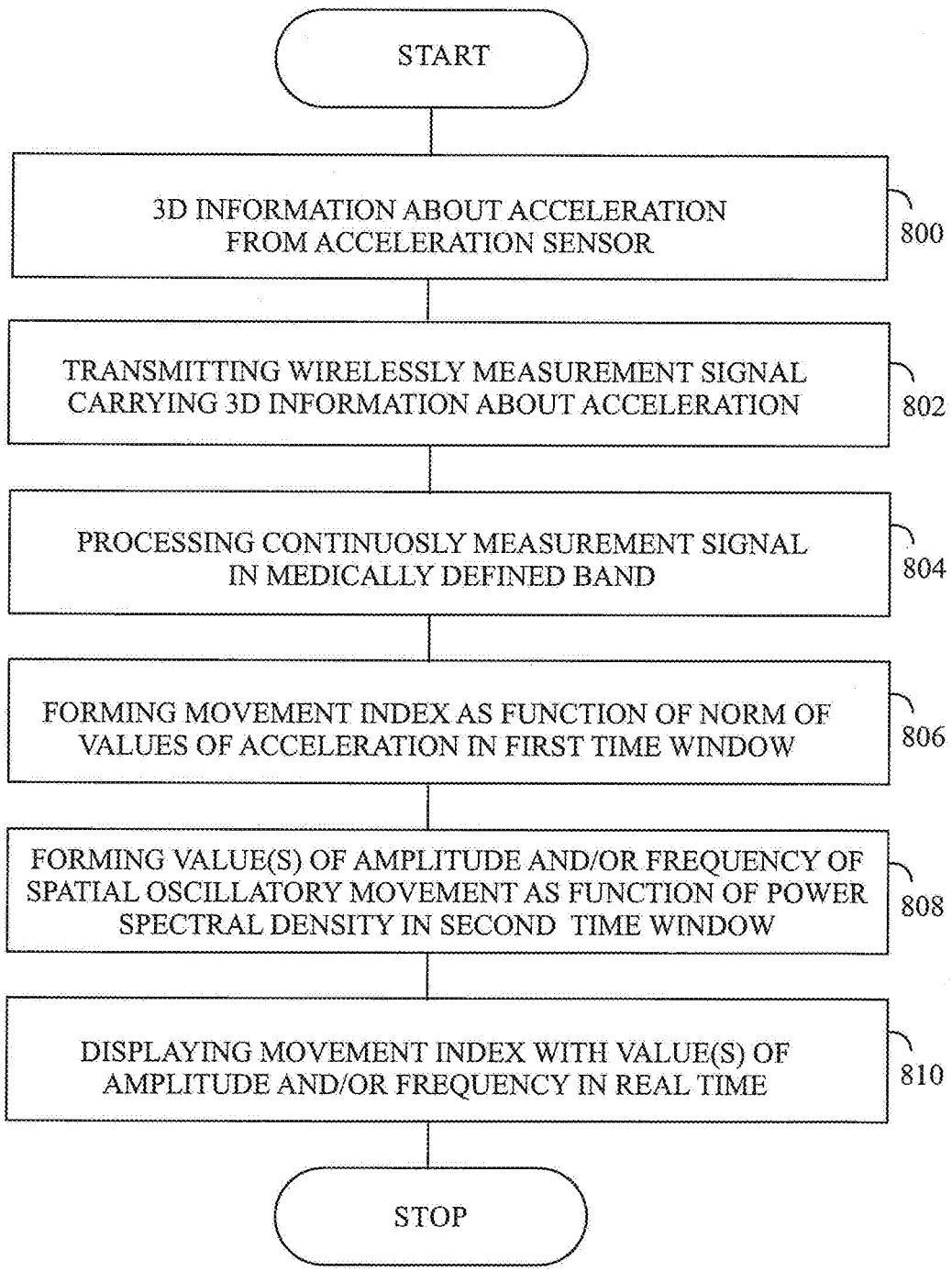
FIG. 8 illustrates of an example of a flow chart of a monitoring method.

FIG. 8 is a flow chart of the monitoring method. In step 800, three-dimensional information about acceleration of a body region 102 of a mammal 10 is provided by an acceleration sensor 100. In step 802, a measurement signal carrying the three-dimensional information about the acceleration is transmitted wirelessly by a transmitter 202, the acceleration sensor 200 and the transmitter 202 being integrated in a common acceleration unit 100, which is attachable to or holdable by the body region 102 of the mammal 10. In step 804, the measurement signal is processed continuously in a medically defined band of a movement of the body region 102 by a processing unit 104. In step 806, a movement index is formed on the basis of a norm of values of acceleration in a first time window of a known duration by the processing unit 104. In step 808, a value of amplitude and/or a value of frequency of the spatial movement is formed on the basis of a power spectral density in second time window of a known duration, by the processing unit 104. In step 810, said movement index with said value of amplitude and/or said value of frequency of the spatial movement is displayed continuously in real time by a display 106.

The method shown in FIG. 8 may be implemented as a logic circuit solution or computer program. The computer program may be placed on a computer program distribution means for the distribution thereof. The computer program distribution means is readable by a data processing device, and it encodes the computer program commands, carries out the measurements and optionally controls the processes on the basis of the measurements.

The computer program may be distributed using a distribution medium which may be any medium readable by the controller. The medium may be a program storage medium, a memory, a software distribution package, or a compressed software package. In some cases, the distribution may be performed using at least one of the following: a near field communication signal, a short distance signal, and a telecommunications signal.

It will be obvious to a person skilled in the art that, as technology advances, the inventive concept can be implemented in various ways. The invention and its embodiments are not limited to the example embodiments described above but may vary within the scope of the claims.

What is claimed is:

1. An apparatus for monitoring movement, wherein the apparatus comprises for continuous real time monitoring:
   an acceleration unit attachable to a body region of a mammal, the acceleration unit comprising a three-dimensional acceleration sensor and a wireless transmitter for transmitting a measurement signal provided by the acceleration sensor continuously, the measurement signal carrying three-dimensional information about acceleration of the body region;
   a processing unit configured to receive the measurement signal transmitted wirelessly, process the measurement signal continuously in a frequency band of a medically defined involuntary oscillatory movement of the body region, form a movement index on the basis of a norm of values of acceleration in a first time window of a known duration, and form a value of amplitude and/or a value of frequency of the spatial movement of the body region on the basis of a power spectral density in a second time window of a known duration, the second time window being longer than the first time window, wherein the movement index defines movement of the mammal at a moment corresponding to the first time window for comparison with movement of the mammal at a different moment; and
   a display configured to display said movement index with said value of amplitude and/or said value of frequency of the spatial movement continuously in real time.

2. The apparatus of claim 1, wherein the processing unit is configured to associate an identification of the mammal with each of said movement index and said value of amplitude and/or said value of frequency; and the display is configured to display the identification and said movement index with said value of amplitude and/or said value of frequency of the spatial movement.

3. The apparatus of claim 1, wherein a maximum mass of the acceleration unit is 50 g.

4. The apparatus of claim 1, wherein the first time window is between about half a second and two seconds, and the second time window is between one second and five seconds, respectively.

5. The apparatus of claim 1, wherein the apparatus comprises a camera configured to capture a video of the mammal, the movement of which is monitored; the processing unit is configured to associate the video with the identification of the mammal; and the display is configured to display said video, and said movement index with said value of amplitude and/or said value of frequency of the spatial movement synchronously with the video.

6. The apparatus of claim 1, wherein the processing unit is configured to store said movement index and said value of amplitude and/or said value of frequency formed on the basis of measurements at a plurality of moments, and present said movement index and said value of amplitude and/or said value of frequency formed at a moment and said movement index and said value of amplitude and/or said value of frequency formed at a different moment for comparison.

7. The apparatus of claim 1, wherein processing unit comprises
   one or more processors; and
   one or more memories including computer program code; and
   the one or more memories and the computer program code are configured to, with the one or more processors, cause apparatus at least to:
   form the movement index on the basis of the norm of the values of acceleration in a first time window of the known duration, and form the value of the amplitude and/or the value of the frequency of the spatial movement on the basis of the power spectral density in the second time window of the known duration.

8. The apparatus of claim 1, wherein a maximum total mass of the acceleration unit attached to a body region is about 10% of a mass of the body region.

9. The apparatus of claim 1, wherein a maximum total mass of the acceleration unit attached to a body region is about 5% of a mass of the body region.

10. A method of monitoring spatial movement, the method comprising:
    providing, by an acceleration sensor, three-dimensional information about acceleration of a body region of a mammal;
    transmitting wirelessly, by a transmitter, a measurement signal carrying the three-dimensional information about the acceleration; the acceleration sensor and the transmitter being integrated in a common acceleration unit, which is attachable to the body region of the mammal;
    receiving, at a processing unit, the measurement signal transmitted wirelessly;
    processing, by the processing unit, the measurement signal continuously in a frequency band of a medically defined involuntary oscillatory movement of the body region;
    forming, by the processing unit, a movement index on the basis of a norm of values of acceleration in a first time window of a known duration;
    forming, by the processing unit, a value of amplitude and/or a value of frequency of the spatial movement of the body region on the basis of a power spectral density in a second time window of a known duration, the second time window being longer than the first time window, wherein the movement index defines movement of the mammal at a moment corresponding to the first time window for comparison with movement of the mammal at a different moment; and
    displaying, by a display, said movement index with said value of amplitude and/or said value of frequency of the spatial movement continuously in real time.

11. The method of claim 10, further comprising associating, by the processing unit, an identification of the mammal with each of said movement index and said value of amplitude and/or said value of frequency; and
    displaying, by the display, the identification and said movement index with said value of amplitude and/or said value of frequency of the spatial movement.

12. The method of claim 10, wherein a maximum total mass of the acceleration unit attached to a body region is about 10% of a mass of the body region.

13. The method of claim 10, wherein a maximum total mass of the acceleration unit attached to a body region is about 5% of a mass of the body region.

14. The method of claim 10, wherein a maximum mass of the acceleration unit is 50 g.

15. The method of claim 10, wherein the first time window is between about half a second and two seconds, and the second time window is between one second and five seconds, respectively.

16. The method of claim 10, wherein the apparatus comprises a camera configured to capture a video of the mammal, the movement of which is monitored, the method further comprising:

associating, by the processing unit, the video with the identification of the mammal; and displaying, by the display, said video, and said movement index with said value of amplitude and/or said value of frequency of the spatial movement synchronously with the video.

17. The method of claim 10, further comprising storing, by the processing unit, said movement index and said value of amplitude and/or said value of frequency formed on the basis of measurements at a plurality of moments, and presenting said movement index and said value of amplitude and/or said value of frequency formed at a moment and said movement index and said value of amplitude and/or said value of frequency formed at a different moment for comparison.

18. The method of claim 10, wherein processing unit comprises one or more processors; and one or more memories including computer program code; and the one or more memories and the computer program code are configured to, with the one or more processors, cause apparatus at least to:

form the movement index on the basis of the norm of the values of acceleration in a first time window of the known duration, and form the value of the amplitude and/or the value of the frequency of the spatial movement on the basis of the power spectral density in the second time window of the known duration.

* * * * *